(12) United States Patent
Plessers et al.

(10) Patent No.: US 7,365,841 B2
(45) Date of Patent: Apr. 29, 2008

(54) METHOD FOR ANALYSIS OF A MOLTEN MATERIAL, DEVICE AND IMMERSION SENSOR

(75) Inventors: Jacques Plessers, Houthalen (BE); Vittorino Tusset, Oupeye (BE); Marc Schyns, Roclenge-sur-Geer (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 142 days.

(21) Appl. No.: 11/422,339

(22) Filed: Jun. 6, 2006

(65) Prior Publication Data
US 2006/0250614 A1 Nov. 9, 2006

Related U.S. Application Data

(63) Continuation of application No. PCT/EP2004/014252, filed on Dec. 15, 2004.

(30) Foreign Application Priority Data

Dec. 17, 2003 (DE) ................. 103 59 447
Feb. 13, 2004 (BE) ................. 2004/0085

(51) Int. Cl.
*G01J 3/443* (2006.01)
(52) U.S. Cl. ................. 356/311; 356/313; 356/318
(58) Field of Classification Search ............... 356/311, 356/313, 318
See application file for complete search history.

(56) References Cited

U.S. PATENT DOCUMENTS 4,986,658 A 1/1991 Kim 5,319,576 A * 6/1994 Iannadrea ................. 702/130
5,369,483 A 11/1994 Wilson
2003/0197125 A1 10/2003 De Saro et al.

FOREIGN PATENT DOCUMENTS

| DE | 3839561 A1 | 5/1990 |
|---|---|---|
| EP | 1 070 953 A1 | 1/2001 |
| GB | 2 154 315 A | 9/1985 |
| WO | 03/081287 A2 | 10/2003 |

* cited by examiner

*Primary Examiner*—F. L. Evans
*Assistant Examiner*—Abdullahi Nur
(74) *Attorney, Agent, or Firm*—Panitch Schwarze Belisario & Nadel LLP

(57) ABSTRACT

A method and device are provided for analysis of a molten material using optical emission spectrometry. The molten material may be, for example, a molten metal, such as casting iron or steel, or slag, glass, or lava. A sensitive element is used having at least one emission spectrometer and at least one excitation device to effect the excitation of the molten material and to enable the partial or complete generation of a radiation to be analyzed by a spectrometer present in the sensitive element. The sensitive element is brought into contact with the molten material and transmits information, which contains analysis elements supplied by the spectrometer. An immersion sensor is also provided for carrying at least part of the device for performing the analysis method.

41 Claims, 2 Drawing Sheets

METHOD FOR ANALYSIS OF A MOLTEN MATERIAL, DEVICE AND IMMERSION SENSOR

CROSS-REFERENCE TO RELATED APPLICATIONS

This application is a continuation of International Application No. PCT/EP2004/014252, filed Dec. 15, 2004, which was published in the German language on Jun. 30, 2005, under International Publication No. WO 2005/059527 A1, the disclosure of which is incorporated herein by reference.

BACKGROUND OF THE INVENTION

The invention relates to a method for analysis of a high-temperature molten material using optical emission spectrometry. It is particularly suitable for the analysis of a molten metal, such as molten iron or steel, but can also be used to analyze slag, glass, lava, or any other fluid, high-temperature material. The invention also relates to a new device for the use of the inventive method for analysis using optical emission spectrometry. The invention furthermore relates to an immersion sensor for analysis of molten materials, particularly metal, slag, or lava melts, or of glass, comprising an immersion carrier, a radiation detector, a radiation guidance system for recording and further transmission of the radiation, and a signal interface located on or in the immersion carrier.

The preferred range of applications of the invention is the analysis of metal, lava, glass, or slag baths, and of other refractory molten materials, wherein the named materials are in a partially or fully molten state.

The areas in which the analysis of the composition of high-temperature molten products is performed are quite wide-ranging, i.e., having a temperature above 300° C., for example molten steel, molten aluminum, molten glass, or molten lava. The methods generally used require the removal of a sample, which is first cooled and then subjected to various analytical procedures after partial or complete cooling.

Different analytical techniques can be used and are selected depending on the components of the composition to be identified qualitatively or dosed quantitatively. This selection is dictated by the practical modalities in connection with operating conditions, such as the physical form in which the material to be analyzed is presented (e.g., steel bath in a steel refinery converter, bath of refractory material in a smelter, molten glass in an oven, or lava in a volcano), and the desired type of operation (e.g., practical access to the material, environment at the analysis location, available time before achieving results of the analytical procedure).

The present description, for purposes of explanation, concentrates on the area of analysis of metallic molten masses, while reserving the application of the method to other high-temperature molten materials.

In the context of analysis of molten metals, emission spectrometry is the most commonly used technique, because it can be performed very quickly, requires only very little work in preparation of samples, and enables the simultaneous dosage of a large number of components. Emission spectrometry is based on the fact that the material to be analyzed is excited in such a way that ionization of the material, of which it consists, is achieved. The radiation emitted is then analyzed in a spectrometer, which separates this radiation into different wavelengths corresponding to the materials present. A distinction is made between different types of spectrometer, wherein the most common in the areas in question are equipped with photomultiplier detectors or with CCD systems (Charged Coupled Device) or CMOS (Complementary Metal Oxide Semiconductors). The equipment for analysis with emission spectrometry is either laboratory equipment or portable equipment for analysis of immobile materials.

The economic interest in the method of spectrometric analysis is known and is commonly used in industry, since it enables the entire chain of metals manufacture to be tracked, controlled, and monitored. The pressure towards profitability naturally makes necessary the search for the simplest and fastest methods, which suitably cost the least relative to the profitability of the manufacturing processes.

In this search for profitability, several methods have been examined for the dosing of fluid metals while omitting the taking of samples, and are currently being developed in the laboratory or in the context of more or less highly developed testing on a pilot line.

The current methods consist of exciting the product remotely, for example using a laser beam, whereby the product then emits an induced radiation due to the excitation of the beam, which is analyzed by an emission spectrometer. The spectrometer is more or less removed from the glowing (radiating) product to be analyzed, and in fact is located according to the practical possibilities of application, for example the working conditions in a steel mill. The radiation proceeding from the product to be analyzed can be guided to the spectrometer in different ways, such as through a glass fiber, through a telescope, etc.

It is known that current developments are underway to miniaturize and simplify spectrometers in which a detector based on CCD technology is used, the costs of which will be low enough to enable profitable industrial use in a production context. The different technologies named above—both those already used in industrial production and those technologies currently under development—are all based on an element which is located outside the object of analysis, in order to create the excitation which generates the radiation to be spectrometrically analyzed. At present, this often requires the use of a laser system which is located in the vicinity of the object of analysis—for example in a metal bath located in a converter. In addition, the aforementioned laser system also requires different targeting equipment to direct the laser beam.

In practice in industrial production, it can be determined that the environmental conditions around the places of production of molten metals, such as steel works, and correspondingly for the analysis of lava around volcanoes, are very aggressive relative to the devices used for their monitoring. In this connection, optical devices are particularly sensitive. The result is that the use of the aforementioned laser equipment presents a source of technical problems, and any development regarding a broad and intensive industrial application of spectrometric analysis methods using excitation from equipment involving the radiation emitted by lasers is often prone to accidents and is very difficult.

Such techniques as immersion sensors for analysis in molten materials are known from International application publication No. WO 03/081287 A2. Here, a carrier tube is disclosed, which is immersed in molten aluminum. Within the carrier tube a lens system is arranged. At the upper end of the tube an optical fiber is arranged, which is connected through an optical system, on the one hand to a spectrograph and on the other hand to a laser. The radiation emitted from the melt is guided through the optical fiber to the spectrograph, and there, the radiation is analyzed in order to derive analytical results pertaining to the composition of the molten aluminum.

BRIEF SUMMARY OF THE INVENTION

An improved method is to be provided for analysis of a molten material using optical emission spectrometry, which is particularly intended for the analysis of a molten metal, such as casting iron or steel, but which is also applicable for the analysis of slag, glass, lava, or other high-temperature, fluid materials.

The object is achieved, according to the present invention, wherein a method is provided for analysis of a molten material using optical emission spectrometry, which is particularly intended for the analysis of a molten metal, such as casting iron or steel, but which is also applicable for the analysis of slag, glass, lava, or other fluid materials having a temperature above 300° C. and preferably above 500° C., in which a so-called "sensitive element" is used, which includes at least an emission spectrometer, essentially characterized in that

- a sensitive element with at least one excitation device is used to effect the excitation of the material to be analyzed and to enable the partial or complete generation of a radiation beam to be analyzed by a spectrometer present in the sensitive element,
- the sensitive element is brought into contact with the material to be analyzed,
- information is recorded, which is designated as an analysis signal and is emitted by the sensitive element between the time of its contact with the molten material to be analyzed and its destruction by melting in the aforementioned material, and the transmitted information contains analysis elements which are produced by a spectrometer present in the sensitive element, and
- from the transmitted analysis signal, either directly upon reading or after processing, at least part of the chemical elemental composition of the material to be analyzed can be derived.

Since the sensitive element used in the method of carrying out the analysis includes not only an emission spectrometer, but also an excitation device for effecting the excitation of the analyzed material and for generation of a part or the entirety of the radiation analyzed by the spectrometer present, the use of that sensitive element represents a solution for the problems associated with the use of an external excitation device, such as a laser, which is located in the vicinity of the material to be analyzed. The method thus comprises the use of a system for self-excitation of the material to be analyzed, such that an emission spectrum is emitted, which can be analyzed by a local spectrometer, i.e., by a spectrometer which is present in the element which is brought into contact with the molten material to be analyzed. These built-in self-excitation devices are integrated into a sensitive element, which is a sensor for one-time use or a disposable sensor.

According to an advantageous embodiment of the inventive method, a modulation technique is used in order to take the practical operational conditions into account, for example a so-called measurement of base radiation used in measurement and control technology.

There is preferably at least one measurement made of the spectrum emitted by the material to be analyzed without excitation of this material. The spectrum of the base radiation obtained in this manner is then subtracted from the spectrum recorded by the sensitive element after excitation of the material to be analyzed. Based on the result of this operation, an analysis signal independent of the base radiation is transmitted by the sensitive element.

According to a further embodiment of the inventive method, before the step of excitation of the material to be analyzed, at least one measurement is performed of the temperature of the material to be analyzed, in order to correct the signal transmitted by the sensitive element. Any deviations (wavelength, amplitude, bandwidth) in the emission lines characteristic for the material after excitation of the material to be analyzed should be taken into consideration independently of the temperature.

According to a further embodiment of the inventive method, there is moreover at least one measurement performed of the spatial position of the location to be analyzed, in order to assess the relevance of its selection for a measurement. This consists in ensuring that it is not less interestingly oriented, for example on the edge of the bath or in the vicinity of an oxidized surface. There is a danger that the analysis of the material located in these places may not be representative of the material located in the bath to be analyzed.

According to a further embodiment of the inventive method, there is at least one excitation device provided for generation of an electrical excitation; the aforementioned excitation device includes preferably at least one charged capacitor equipped with an interruption device. The capacitor may optionally be supplied by a battery and can generate between 1 and 2000 discharges, wherein each discharge must last at least 10 nsec (nanoseconds) and have an intensity of at least 0.01 amperes.

According to a further embodiment of the method, at least one excitation device is provided for generation of a chemical excitation, preferably with a fluid quantity of preferably less than 1000 ml. The excitation device is brought into contact with the material to be analyzed in such a way that a high-energy chemical reaction results, which effects the excitation of the material to be analyzed and generates radiation. The radiation is analyzed by a spectrometer present in the sensitive element, wherein this is preferably an explosive chemical reaction.

According to a further embodiment of the inventive method, the excitation device includes moreover a container for the fluid used for the excitation by chemical reaction. The container has as its object the modulation of the duration of contact between the material to be analyzed and the excitation device present or the excitation material. The modulation optionally occurs by management of the using up and then the destruction of one or more components of the spectrometer present at the location and used for analysis of the radiation beam. In the aforementioned case, this consists in using a container as an excitation device. The container is equipped with a device designated as an explosion valve, which is constructed of a metal or a metallic alloy whose melting temperature exceeds the melting temperature of the metal to be analyzed by at least 10° C. In the case of ULC steels, for example, a steel dosed with tungsten can be used for the valve.

According to a further preferred embodiment of the inventive method, in which the material to be analyzed is a molten metal, the excitation device is chemical in nature and uses a fluid—preferably water—wherein the minimum fluid volume used is preferably 0.01 ml.

The present invention relates also to a device for carrying out the inventive method. The device is essentially characterized in that the sensitive element, brought into contact with the molten material to be analyzed, includes a jacket at least partially enclosing the aforementioned sensitive element. The jacket is preferably made of a soluble (under operating conditions) material, preferably vermiculite. According to a practical embodiment of the device, the jacket is geometrically arranged such that the destruction of the sensitive element by melting is delayed. The geometry preferably improves the bringing into contact of the sensitive part of the spectrometer with the material to be analyzed—preferably a molten metal.

According to a further embodiment of the device, the element to be brought into contact with the molten metal to be analyzed is contained in an enclosure whose interior atmosphere is controlled. This atmosphere comprises a gas or a gas mixture, preferably containing nitrogen and/or argon, or is placed under vacuum, preferably at a pressure of at least $10^{-1}$ mm Hg+/−10% in case of a vacuum.

The invention does not require the presence of external systems (laser systems or others) in order to effect the excitation of the material of the object to be analyzed. Using the inventive method, the devices for spectrometric analysis can be simplified and the associated economic costs reduced.

The object is further achieved with an immersion sensor for analysis, particularly of molten metals. The immersion sensor comprises an immersible carrier, a radiation detector, a radiation guide system for the recording and further transmission of radiation, and a signal interface located on or in the immersible carrier. The radiation detector and at least a part of the radiation guide system are located on or in the immersible carrier, and the signal interface is connected to the radiation detector. This significantly simplifies the further signal transmission, since the optical radiation emitted by the molten metal can already be converted at or in the immersible carrier into electrical signals, which can be retransmitted in many different ways. The radiation detector need no longer be arranged for long-term use. After the measurement it loses its function and can thus be built very simply and cost-effectively. Servicing of the radiation detector is no longer necessary.

Preferably, the radiation detector has a device for the recording of radiation and for its conversion into electrical signals. In particular, it is practical to design the radiation detector for the recording and conversion of visible light, ultraviolet radiation, infrared radiation, X-rays and/or microwave radiation into electrical signals. This allows all types of optical or other radiation to be recorded and made usable for analysis of the melt. It is particularly expedient for the immersible carrier to be constructed as a tube in which the individual parts are arranged, since it is thereby possible to better ensure the protection of individual parts during transport. It is also expedient for the immersible carrier to be made of a material consumable in molten metal, particularly an organic material.

It is furthermore advantageous to construct the signal interface as an electrical or optical coupling or as a transmitter (for the wired or wireless transmission of signals). It is correspondingly possible to couple externally impinging optical signals into the radiation guide system, retransmit signals coming from the radiation detector (electrical or optical signals) over wire or cable connections, or even through the air with a transmitter. In particular, this makes it possible to disconnect the immersible carrier easily from the external systems after use and to dispose of it. A new immersible carrier is then connected to lines connected to the external systems (computer, laser for radiation preparation, radio segments, or other systems) via the coupling part. The immersible carrier is preferably connected to a mechanical coupling, preferably for the attachment of a carrier lance. Such carrier lances are common in metallurgy for the holding of measurement devices. Signal lines run inside the carrier lance.

For the case that the signal interface is constructed as a transmitter, the signals emitted from the radiation detector can be transmitted via radio to a computer. Here, it is basically also possible to provide signal evaluation in a component with the radiation detector, so that only the results are retransmitted. It is also conceivable to convert electrical signals arriving at or in the immersible carrier into optical signals. In this case, the signals arriving at the immersible carrier could be transmitted wirelessly and cablelessly via radio, wherein the radio signals are converted into optical signals. This would make a contact-free measurement possible. A fixed connection between the sensor and the evaluation device or a signal preparation device would be superfluous, since it is possible to provide sufficiently cost-effective, small, and powerful components for this purpose.

It is expedient to arrange a signal amplifier and/or a processor for signal evaluation on or in the immersible carrier. It is furthermore expedient for the radiation guide system to have optical and/or magnetic lenses, optical fibers, mirrors, a spark discharge gap, and/or shutters. It is also practical to locate the system for generation of spark discharge or a different radiation emission system on or in the immersible carrier. Advantageously, an optical spectrometer, an X-ray spectrometer, and/or a mass spectrometer can be arranged on or in the immersible carrier.

It can make sense to provide a gas-conducting device on or in the immersible carrier, with which the surface of the molten material to be analyzed can be blown clear, so that the radiation can be focused onto the surface to be measured or a spark can be generated on it.

In the case where the immersible carrier is constructed as a tube, it is sensible to provide a gas-conducting device inside the tube, in order to prevent the molten material from penetrating into the tube upon immersion of the immersion sensor. In particular, materials which melt at high temperatures, such as cryolite melts, iron or steel melts, or even glass, lava, or copper melts can be analyzed well in the manner described above.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
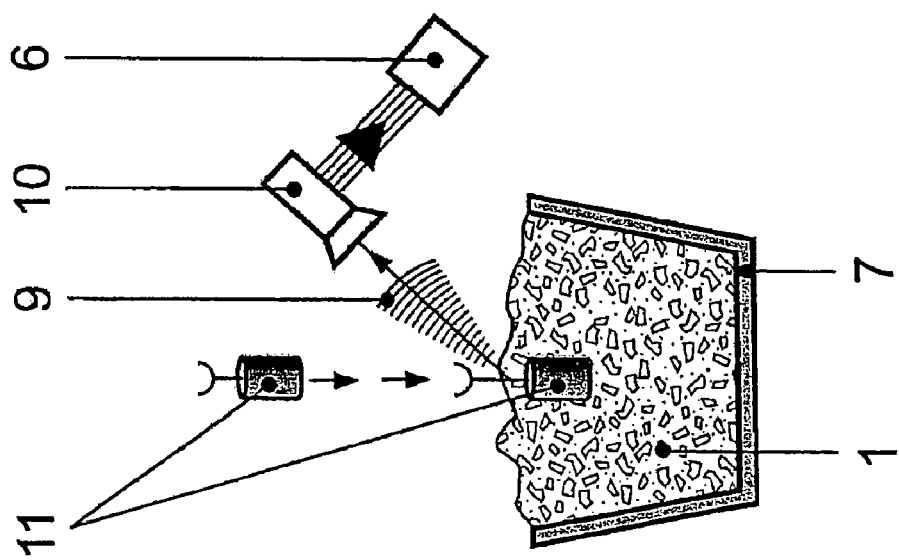
FIG. 1 is a schematic, side sectional view illustrating one embodiment of a basic structure and method according to the present invention.

FIG. 1 illustrates a method and device as it is in development or in an industrial pilot stage. There are to be seen here the metal 1, or any solid or fluid material to be analyzed, in a container 7, and a laser system 2, whose beam 3 strikes the metal 1 and there effects such a heating that radiation 4 is emitted therefrom. The radiation 4 is at least partly directed to a spectrometer 5, which is connected with different analysis and/or signal processing systems 6, which enable the interpretation of the information/analysis signal contained in the radiation 4, in order to derive the analysis of the metal 1 therefrom.

Figure 2:
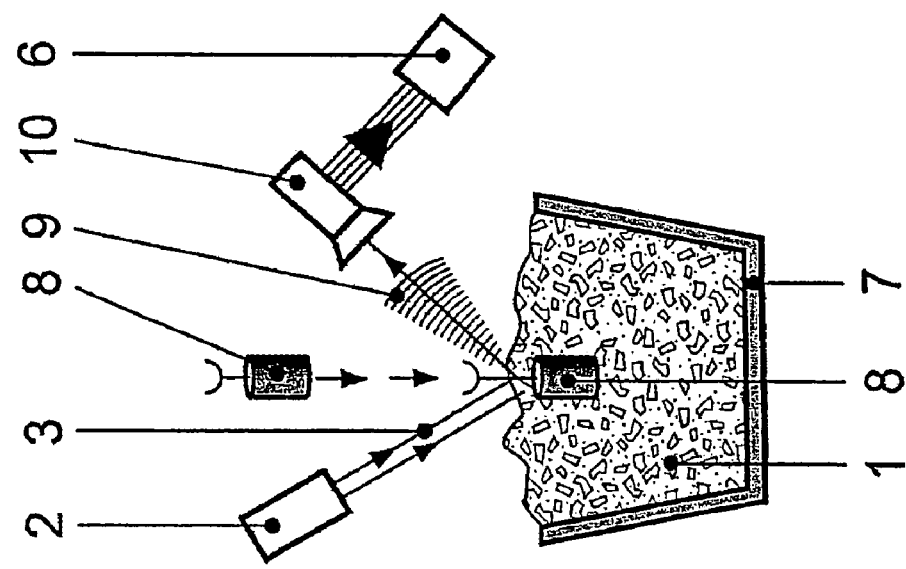
FIG. 2; is a schematic, side sectional view illustrating another embodiment of a basic structure and method according to the present invention

FIG. 2 illustrates an alternative method and device, which can be used for the analysis of a molten metal bath. There are to be seen here the material to be analyzed, which is a metal bath 1 contained in a container 7, along with a CCD spectrometer 8 which is brought into contact with the metal bath 1. The spectrometer 8 is destroyed after the passage of a certain time by melting in the analyzed bath 1. The spectrometer 8 is equipped with a radiation detector, wherein the radiation may first be divided into different components with a grid or a crystal. The aforementioned detector may be a CCD detector or the like, which is equipped with a transmitter system that transmits the data supplied by the detector to an antenna 10 for further analysis and/or operational processing in a suitable analysis and/or signal processing system 6.

The use of the device illustrated in FIG. 2 proceeds by inducing an excitation in the metal bath 1 to be analyzed using the excitation device 2, which is generally a laser, that emits the beam 3. The beam strikes the metal bath 1 at a location lying in the vicinity of spectrometer 8, such that this records and analyzes the radiation induced by beam 3 from the excitation laser 2 and originating from the bath 1. The result of the analysis operation by spectrometer 8 is transmitted through a transmission path 9 (for example in the form of waves via radio or via cable) to a recording device/antenna 10, which may be suitable for storage of the information/analysis signal or for its retransmission to an analysis and/or signal processing system 6, which enables an interpretation of the analysis of the induced radiation to determine the chemical composition of the metal bath. The execution of the entire analysis and transmission procedure is, of course, carried out before destruction of the aforementioned spectrometer 8 by melting.

Figure 3:
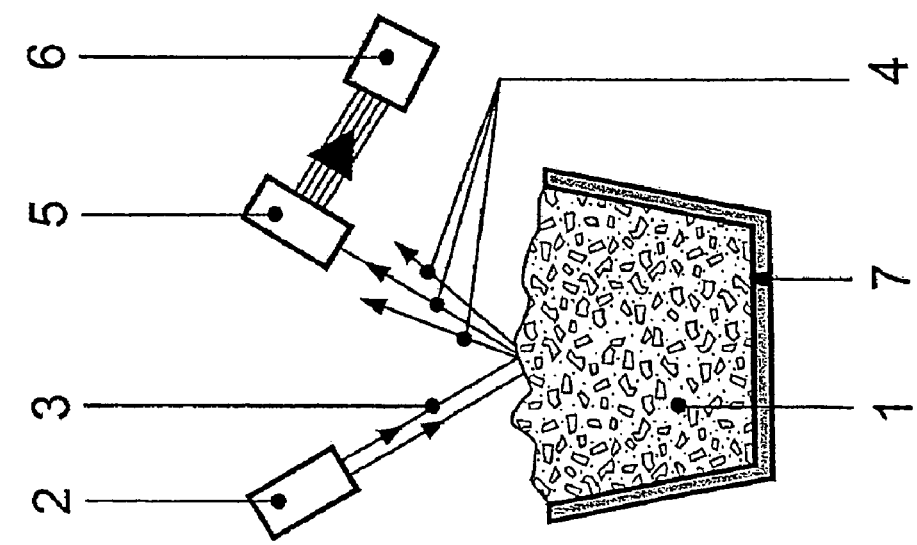
FIG. 3 is a schematic, side sectional view illustrating a further embodiment of a basic structure and method according to the present invention.

For the analysis of the metal batch 1 shown in FIG. 3, the bath is contained in container 7, which is preferably a converter, a steel mill crucible, or a melting and/or reduction oven. A sensitive element 11 is placed in the container, wherein the sensitive element includes at least one spectrometer and a system for the self-excitation of the metal making up the bath 1 to be analyzed. The excitation is then manually, automatically, or otherwise triggered when the sensitive element 11 is in contact with the bath 1 to be analyzed. Via the recording device/antenna 10, a signal 9 originating from the sensitive element 11 is recorded, which can be processed by an analysis and/or signal processing system 6 for the interpretation of the results of measurements performed by a spectrometer located in sensitive element 11. This results in a simplification of the installation due to the omission of any excitation system outside the sensitive element, which is brought into contact with the fluid metal. Only the equipment remains which is used for introduction of the sensitive element into the metal bath and devices for the recovery of the data originating from the sensitive element via radio or physically, such as via a cable connection.

Figure 4:
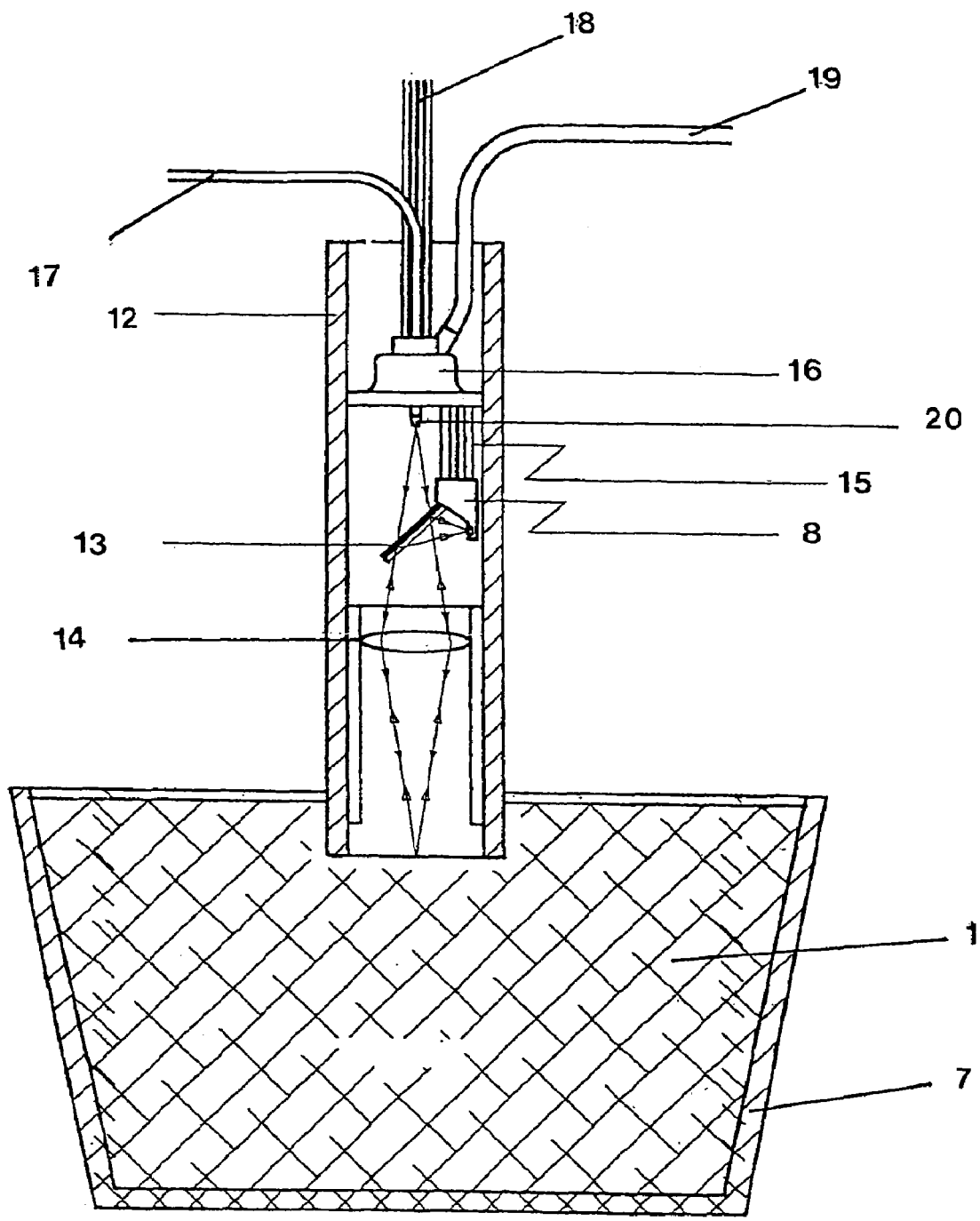
FIG. 4 is a schematic side sectional view of an immersion sensor according to the invention, immersed in a molten metal.

In the embodiment of the invention shown in FIG. 4, an immersion sensor is partially immersed in a container/crucible 7 with molten iron 1. The immersible carrier 12 is constructed as a cardboard tube in which the radiation guide system is arranged with a one-way mirror 13 and a lens 14. In the tube there is further arranged a spectrometer 8, which records the radiation coming from the molten iron 1 and converts it into electrical signals. The electrical signals are retransmitted to a coupling 16 via signal lines 15. The coupling 16 is used to connect the immersion sensor with external power supply systems.

For this purpose, a laser source is connected to the connector/coupling 16 via an optical fiber 17, signal cables 18 connect the immersion sensor with a computer, and a gas line 19 enables the supply of gas into the tube (the immersible carrier 12). The tube itself constitutes the gas line between the coupling 16 and the molten iron 1. The optical fiber 17 is connected to a light aperture 20. Laser light is focused through the light aperture 20 by the mirror 13 and the lens 14 onto the molten iron 1. The light reflected from the molten iron 1 is directed by the mirror 13 onto the signal input of the spectrometer 8. For this purpose, mirror 13 is constructed as a one-way mirror.

Besides these concretely described embodiments, the embodiments already described above are likewise conceivable. In the end of the tube facing away from the immersion end, a carrier lance can be inserted, on which the tube can be held during the immersion procedure.

The industrial areas in which the present analysis method by emission spectrometry can be used are quite numerous. They are not merely limited to the handling operations in a steel mill, but can also be used for monitoring by analysis of the composition for other metallurgical baths, possibly serving for baths for the separation of metal as in galvanization. A significant productivity increase can be expected, since at no point in time is an interruption of the industrial manufacturing process required for carrying out the analysis by optical emission spectrometry, and thus no time loss occurs.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for analysis by optical emission spectrometry of a molten material having a melting temperature above 300° C., the method comprising:
    providing a sensitive element having at least one excitation device to effect excitation of the molten material and to enable at least partial generation of a radiation to be analyzed by at least one emission spectrometer present in the sensitive element,
    bringing the sensitive element into contact with the molten material,
    recording an analysis signal transmitted by the sensitive element between a point in time of bringing the sensitive element into contact with the molten material and a point of time of destruction of the sensitive element by melting in the molten material, wherein the transmitted analysis signal contains analysis elements supplied by the spectrometer, and determining from the transmitted analysis signal, directly upon reading or after processing, at least a partial chemical elemental composition of the molten material.

2. The analysis method according to claim 1, further comprising using a modulation technique.

3. The analysis method according to claim 1, further comprising performing at least one measurement of a first spectrum of base radiation emitted by the molten material without excitation of the molten material, and subtracting the first spectrum thus obtained from a second spectrum taken by the sensitive element after excitation of the molten material.

4. The analysis method according to claim 1, further comprising performing at least one measurement of a temperature of the molten material to correct the transmitted analysis signal.

5. The analysis method according to claim 4, wherein the at least one measurement of the temperature of the molten material is performed before the excitation of the molten material.

6. The analysis method according to claim 1, further comprising performing at least one measurement of a spatial position of a location of the analysis to determine its relevance.

7. The analysis method according to claim 1, wherein the at least one excitation device generates an electrical excitation.

8. The analysis method according to claim 7, wherein the at least one excitation device generates from 1 to 2000 discharges, each discharge lasting at least 10 nanoseconds and having an intensity of at least 0.01 amperes.

9. The analysis method according to claim 1, wherein the at last one excitation device generates a chemical excitation.

10. The analysis method according to claim 9, wherein the at least one excitation device contains a quantity of fluid less than 1000 ml, and wherein the at least one excitation device is brought into contact with the molten material in such a way that a high-energy chemical reaction occurs to effect the excitation of the molten material which generates a radiation to be analyzed by the spectrometer.

11. The analysis method according to claim 10, wherein the chemical reaction is explosive in nature.

12. The analysis method according to claim 10, wherein the at least one excitation device includes a container for the fluid, wherein the container allows modulation of duration of contact between the molten material and the at least one excitation device.

13. The analysis method according to claim 12, wherein the modulation occurs by consumption and subsequent destruction of one or more components of the spectrometer.

14. The analysis method according to claim 1, wherein the at least one excitation device generates a chemical excitation and contains a fluid having a minimum fluid volume of 0.01 ml.

15. The analysis method according to claim 14, wherein the fluid is water.

16. The analysis method according to claim 1, wherein the molten material is a molten metal selected from iron and steel.

17. The analysis method according to claim 1, wherein the molten material is slag, glass, or lava.

18. A device for carrying out the analysis method according to claim 1,
wherein the sensitive element includes a jacket, which at least partially surrounds the sensitive element and comprises a soluble material.

19. The device according to claim 18, wherein the soluble material comprises vermiculite.

20. The device according to claim 18, wherein the jacket is constructed in such a way that geometry of the jacket delays the destruction of the sensitive element by melting.

21. The device according to claim 18, wherein the jacket is constructed in such a way that geometry of the jacket promotes bringing a sensitive part of the spectrometer into contact with the molten material.

22. The device according to claim 18, wherein the sensitive element is contained in an enclosure with a controlled interior atmosphere.

23. The device according to claim 22, wherein the enclosure contains an atmosphere comprising at least one gas selected from nitrogen or argon.

24. The device according to claim 22, wherein the enclosure is set under vacuum.

25. The device according to claim 24, wherein the enclosure is set under vacuum at a pressure of at least $10^{-1}$ mm Hg +/−10%.

26. The device according to claim 18, wherein the at least one excitation device is of electrical construction and includes at least one charged capacitor equipped with an interruption device.

27. The device according to claim 18, wherein the at least one excitation includes at least one battery.

28. An immersion sensor for analysis of molten materials, particularly metal, slag, lava or glass melts, the sensor comprising an immersible carrier, a radiation detector, a radiation guide system for recording and retransmission of radiation, and a signal interface, wherein the radiation detector, the signal interface and at least a part of the radiation guide system are arranged on or in the immersible carrier, the signal interface is connected with the radiation detector, and the immersible carrier is constructed of a material consumable in the molten material.

29. An immersion sensor for analysis of molten materials, particularly metal, slag, lava or glass melts, the sensor comprising an immersible carrier, a radiation detector, a radiation guide system for recording and retransmission of radiation, and a signal interface, wherein the radiation detector, the signal interface and at least a part of the radiation guide system are arranged on or in the immersible carrier, the signal interface is connected with the radiation detector, and the immersible carrier is connected with a mechanical coupling.

30. The immersion sensor according to claim 28, wherein the radiation detector includes a device for recording of radiation and for conversion into electrical signals.

31. The immersion sensor according to claim 30, wherein the radiation detector is installed for the recording and conversion of visible light, ultraviolet radiation, infrared radiation, X-rays, and/or microwave radiation into electrical signals.

32. The immersion sensor according to claim 28, wherein the immersible carrier is constructed as a tube.

33. The immersion sensor according to claim 29, wherein the immersible carrier is constructed of a material consumable in the molten material.

34. The immersion sensor according to claim 28, wherein the signal interface is constructed as an electrical or optical coupling or as a transmitter.

35. The immersion sensor according to claim 28, wherein the immersible carrier is connected with a mechanical coupling for coupling to a carrier lance.

36. The immersion sensor according to claim 28, further comprising a signal amplifier and/or a processor for signal evaluation arranged on or in the immersible carrier.

37. The immersion sensor according to claim 28, wherein the radiation guide system includes optical and/or magnetic lenses, optical fibers, mirrors, a spark discharge gap, an excitation device for chemical excitation, and/or shutters.

38. The immersion sensor according to claim 28, further comprising an optical spectrometer, an X-ray spectrometer, and/or a mass spectrometer arranged on or in the immersible carrier.

39. The immersion sensor according to claim 28, further comprising a radiation emitter arranged on or in the immersible carrier.

40. The immersion sensor according to claim 28, further comprising a gas line device arranged on or in the immersible carrier.

41. The immersion sensor according to claim 40, wherein the gas line device includes a gas line and a line coupling.

* * * * *